(12) United States Patent
Annis

(10) Patent No.: US 7,023,950 B1
(45) Date of Patent: Apr. 4, 2006

(54) METHOD AND APPARATUS FOR DETERMINING THE POSITION OF AN X-RAY CONE BEAM PRODUCED BY A SCANNING ELECTRON BEAM

(76) Inventor: Martin Annis, 66 Church St., Cambridge, MA (US) 02138

(*) Notice: Subject to any disclaimer, the term of this patent is extended or adjusted under 35 U.S.C. 154(b) by 0 days.

(21) Appl. No.: 11/054,596

(22) Filed: Feb. 9, 2005

Related U.S. Application Data

(60) Provisional application No. 60/543,472, filed on Feb. 11, 2004.

(51) Int. Cl.
*H01J 35/08* (2006.01)
*H01J 35/30* (2006.01)

(52) U.S. Cl. .................... 378/2; 378/119; 378/124; 378/137; 378/143; 378/146; 378/207

(58) Field of Classification Search .................... 378/2, 378/9, 10, 12, 57, 98.6, 119, 124, 137, 143, 378/146, 207
See application file for complete search history.

(56) References Cited

U.S. PATENT DOCUMENTS

| | | | | |
|---|---|---|---|---|
| 4,352,021 A | * | 9/1982 | Boyd et al. ............. | 378/12 |
| 5,148,462 A | * | 9/1992 | Spitsyn et al. ............. | 378/143 |
| 5,548,630 A | * | 8/1996 | Hell et al. ............. | 378/137 |
| 5,550,378 A | * | 8/1996 | Skillicorn et al. ............. | 250/367 |
| 5,633,906 A | * | 5/1997 | Hell et al. ............. | 378/10 |
| 5,696,806 A | * | 12/1997 | Grodzins et al. ............. | 378/86 |
| 5,761,268 A | * | 6/1998 | Hell et al. ............. | 378/137 |
| 5,841,831 A | * | 11/1998 | Hell et al. ............. | 378/19 |
| 6,009,146 A | * | 12/1999 | Adler et al. ............. | 378/98.6 |
| 6,377,660 B1 | * | 4/2002 | Ukita et al. ............. | 378/143 |
| 6,421,420 B1 | * | 7/2002 | Grodzins ............. | 378/98.6 |
| 6,628,745 B1 | * | 9/2003 | Annis et al. ............. | 378/21 |
| 6,785,360 B1 | * | 8/2004 | Annis ............. | 378/137 |

* cited by examiner

*Primary Examiner*—Allen C. Ho
(74) *Attorney, Agent, or Firm*—Altman & Martin

(57) ABSTRACT

A Laminography system with x-ray source and a detector assembly. The x-ray source uses a narrow, deflected pencil beam to scan to a linear target. An x-ray cone beam detected by the detector assembly is produced where the electron beam strikes the target. The target is a layer of high-emitting material that is partitioned with narrow regions of low-emitting material, where the low flux intensity is sufficiently low to be easily distinguished from the flux intensity of the high-emitting material. The target may be constructed as a discontinuous layer of high-emitting material applied to a substrate of low-emitting material, or as strips of low-emitting material applied to a continuous layer of high-emitting material.

6 Claims, 2 Drawing Sheets

METHOD AND APPARATUS FOR DETERMINING THE POSITION OF AN X-RAY CONE BEAM PRODUCED BY A SCANNING ELECTRON BEAM

CROSS-REFERENCES TO RELATED APPLICATIONS

The applicant wishes to claim the benefit of U.S. Provisional Patent Application No. 60/543,472, filed Feb. 11, 2004 for SEGMENTED X-RAY SOURCE in the name of Martin Annis.

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM LISTING COMPACT DISK APPENDIX

Not Applicable

BACKGROUND OF THE INVENTION

1. Field of the Invention

The present invention relates to laminography or computed tomography imaging and more particularly to locating the exact location of the source of the x-ray beam at a particular point in time.

2. Description of the Related Art

U.S. Pat. No. 6,628,745, issued to the present applicant, describes an x-ray source with an electron source that provides a pencil beam of electrons, a beam directing assembly that directs the pencil beam along a line that strikes a target. As the electron beam moves along the target, a traveling cone beam of x-rays is formed at the intersection point of the electron beam with the target. This cone beam can be collimated into a fan beam by use of a slit collimator adjacent to the target.

In order to use the system to form Laminography or computed tomography (CT) images, it is necessary to know with precision where the electron beam strikes the x-ray target at each instant of time so that the precise location of the source of the x-ray beam is known. Typically, the beam directing assembly is designed to move the beam in a linear and stable fashion over the target. However, there is always the possibility that the motion of the electron beam will drift and not be precisely at the required location for each period of time. This drift can be caused by, for example, external magnetic fields such the Earth's magnetic field, by a mechanical jarring of the system, or by temperature changes.

BRIEF SUMMARY OF THE INVENTION

An object of the present invention is to provide a method and apparatus for more precisely determining the source location of the x-ray cone beam in a Laminography system.

The present invention is a method and apparatus for determining the location of the source of the x-ray cone beam on the x-ray target. With this knowledge of particular locations, it is possible using well-known methods to correct the deflection of the electron beam appropriately.

A Laminography system comprises an x-ray source and a detector assembly. The x-ray source uses a narrow pencil beam directed to a linear target. A magnetic deflector deflects the electron beam so that it scans in an x-ray source line along the target. An x-ray cone beam is produced where the electron beam strikes the target. The cone beam is detected by a detector assembly.

The target is a layer of high-emitting material that emits an x-ray cone beam of substantial flux intensity when struck by the electron beam. The high-emitting material is partitioned with narrow regions of low-emitting material. When the electron beam strikes a low-emitting region, a low flux intensity x-ray cone beam is generated. The low flux intensity is sufficiently low to be easily distinguished from the flux intensity of the high-emitting material.

Any construction that produces low-emitting regions in the target may be employed. In one construction, the target is a discontinuous layer of high-emitting material applied to a substrate of low-emitting material. In another construction, the target is a continuous layer of high-emitting material with strips of low-emitting material applied at the desired locations for the low-emitting regions.

Other objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein.

DETAILED DESCRIPTION OF THE INVENTION

The present invention is a method and apparatus for improving the precision of a Laminography or CT imaging system by determining more precisely the location of the x-ray source at several times while the x-ray source while it traverses across the x-ray target.

Figure 1:
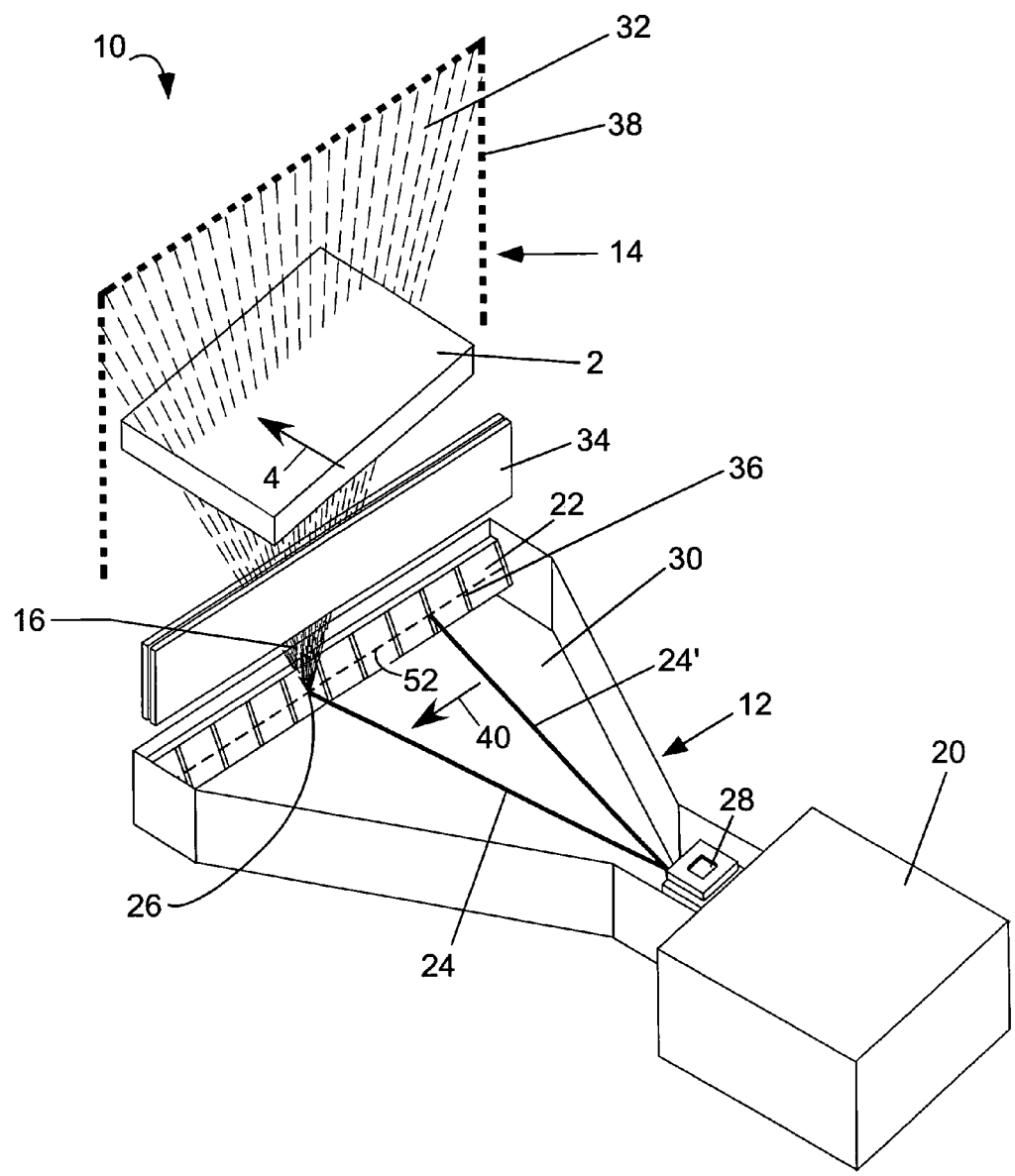
FIG. 1 is a perspective view of a schematic diagram of a Laminography system employing the present invention.

A Laminography system 10 incorporating the present invention is shown in FIG. 1. The system 10 comprises a source/detector assembly that includes an x-ray source 12 and a detector assembly 14 fixed relative to each other. The object being inspected 2 moves, preferably linearly, between the x-ray source 12 and detector assembly 14, as at 4.

An x-ray source 12 that can be employed by the present invention is disclosed in U.S. Pat. No. 6,628,745, incorporated herein by reference. The x-ray source 12 uses a narrow pencil beam 24 of high-energy electrons from a DC source of electrons 20 through a vacuum chamber 30 and directed to a linear target 22. The target 22 may be a thin layer of gold plated onto a suitable substrate material, such as copper. A magnetic deflector 28 deflects the electron beam 24 so that it scans in an x-ray source line 52 along the linear target 22, as at 40, striking the target 22 continuously along the x-ray source line 52. An x-ray cone beam 16 is produced where the electron beam 24 strikes the target 22. This x-ray cone beam source 26 moves continuously to produce a moving cone beam 16 along a line 52. The x-ray cone beam 16 exits the vacuum chamber 30 through a thin window located at the top of the vacuum chamber 30 just below the slit collimator 34. A collimator 34 produces a fan beam 32 from the cone beam 16. The fan beam 32 penetrates the object 2 and is detected by the individual detectors 38 of the detector assembly 14.

Each detector 38 in the detector row 14 is sampled many times, on the order of 1000 times, while the electron beam 24 moves across the target 22. This large amount of data is required to implement the Laminography algorithm. It is necessary to know precisely where the x-ray cone beam source 26 is located at every instant of time in order for the Laminography algorithm to be accurately implemented. The location of the cone beam source 26 is determined by the location of the electron beam 24 on the target 22 as it sweeps across the target 22. For a variety of reasons, this electron beam sweep may not be completely stable and may vary both in the short term and long term. It is therefore desirable to have a precise measurement of the location of the cone beam source 26 at several locations as the electron beam 24 sweeps across the target. These precise measurements are used to correct the position of the cone beam 16 during the computation of the Laminography algorithm.

The target 22 is composed of a layer of high-emitting material 42 that emits an x-ray cone beam 16 of substantial flux intensity when struck by the electron beam 24. In order to determine the precise location of the cone beam source 26, the present invention partitions the high-emitting material 42 with narrow regions 36 of low-emitting material. The result is a series of high-emitting regions 50 separated by narrow low-emitting regions 36. When the electron beam 24' strikes a low-emitting region 36, an x-ray cone beam of substantially lower flux intensity relative to the flux intensity from the high-emitting material 42 is generated. In the present specification, a high-emitting material is a material that emits x-rays at a flux intensity that is adequate for penetrating and imaging the object being inspected. These high-emitting materials are typically higher atomic number materials such as gold or tungsten. A low-emitting material is a material that emits x-rays at a flux intensity that is sufficiently low to be easily distinguished from the flux intensity of the high-emitting material. This material is of lower atomic number, preferably carbon, although other materials can be used that offer sufficient contrast to be distinguishable from the high-emitting materials.

The low-emitting regions 36 are perpendicular to the scanning beam line 52 and are just wide enough to be easily detected by the detector assembly 14. For example, if the spatial resolution of the system is 2 mm, the low-emitting regions 36 can be 1 mm wide. These low-emitting regions 36 are seen by every one of the detectors 38 at a lower intensity in either a Laminography or a CT image, sufficient to be identified electronically by the system. The relative paucity of x-rays from these narrow low-emitting regions 36 is not seen in the resulting CT or laminography images since, in neither case, are transmission images produced.

Figure 2:
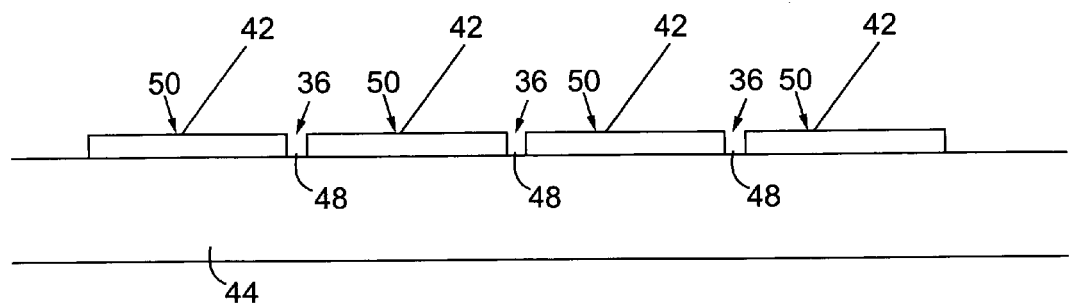
FIG. 2 is a cross-sectional view of one construction of the x-ray source target of the present invention.

The present invention contemplates that any construction that produces low-emitting regions 36 in the target 22 may be employed. In one construction, shown in FIG. 2, the target 22 is a discontinuous layer of high-emitting material 42 applied to a substrate 44 of low-emitting material, but high thermal conductivity and high melting point material. For example, the high-emitting material is gold and is applied to a low-emitting heat sink material, such as aluminum/copper laminate. The discontinuities 48 in the high-emitting material 42 are where the low-emitting regions 36 are desired.

Figure 3:
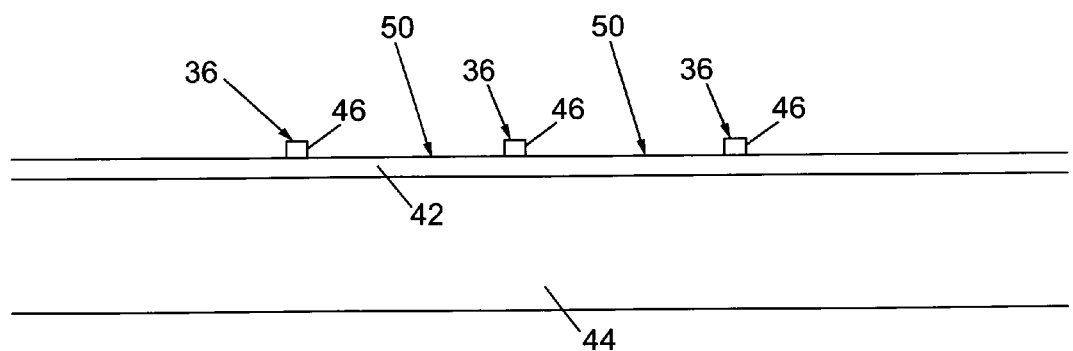
FIG. 3 is a cross-sectional view of another construction of the x-ray source target of the present invention.

In another construction, shown in FIG. 3, the target 22 is a continuous layer of high-emitting material 42 on a substrate 44 where the low-emitting regions 36 are formed by applying strips 46 of low-emitting material, such as carbon, to the high-emitting material 42 at the desired locations for the low-emitting regions 36. The carbon strips may be plated or evaporated and can be quite thin. The advantage of using carbon is that the emission of x-rays is approximately proportional to the atomic number of the material, so the carbon low-emitting regions produce very much less x-ray flux than the aluminum low-emitting regions of the construction of FIG. 2, providing better visibility of the low-emitting regions 36.

Knowing the precise locations of the low-emitting regions 36 on the target 22 permits interpolation of the location of the cone beam 16 between the low-emitting regions 36. The number of low-emitting regions 36 is chosen to be the minimum number that is sufficient to locate the cone beam 16 to the desired degree of precision. The manner of doing this is well known to those practiced in the art. The desired degree of precision depends on the desired spatial resolution of the Laminography images.

The procedure described above to precisely locate the x-ray cone beam source 26 at several times along the x-ray source line 52 is preferably accomplished without an object 2 in the x-ray fan beam 32. An object 2 in the fan beam 32 may make it difficult to identify the low-emitting regions 36 against the background of the high-emitting regions 50. Therefore it is preferable to accomplish the required corrections in the period between inspections when there is nothing in the fan beam 32. This can be done rapidly since the various corrections are done electronically.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, are hereby incorporated by reference.

Thus it has been shown and described a method for determining the position of an x-ray cone beam produced by a scanning electron beam which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

I claim:

1. A system for inspecting an object with an improved method of locating the position of an x-ray source, said system comprising:
   (a) an electron source that provides a pencil beam of electrons;
   (b) an electromagnet assembly that receives said pencil beam of electrons and that directs said pencil beam to form a scanning beam;
   (c) a linear target that is struck by said scanning beam along an x-ray source line, said target having high-emitting regions that produce high-flux-intensity x-ray cone beams from cone beam sources in said x-ray source line when struck by said scanning beam and low-emitting regions that produce low-flux-intensity x-ray cone beams from cone beam sources in said x-ray source line when struck by said scanning beam, said high flux intensity being distinguishable from said low flux intensity, and said low-emitting regions having known locations;
   (d) an assembly of x-ray detectors that receive said high-flux-intensity cone beams and said low-flux-intensity cone beams and that is located in a plane that includes the x-ray source line, said assembly of detectors and said x-ray cone beam sources forming a moving fan beam of detected x-rays, and said assembly of detectors providing signals corresponding to the flux intensity of said detected x-rays; and
   (e) a processor that receives said signals and determines the precise positions of said x-ray cone beam sources at measured time intervals by interpolating between the times corresponding to low-emitting regions.

2. The system of claim 1 further comprising a slit collimator that receives said x-ray cone beams and generates a fan beam in a plane directed to said assembly of x-ray detectors.

3. The system of claim 1 wherein said object is between said target and said assembly of x-ray detectors.

4. The system of claim 1 wherein said target is composed of discrete regions of high-emitting material on a low-emitting substrate.

5. The system of claim 1 wherein said target is composed of low-emitting material applied to high-emitting material at said low-emitting regions.

6. The system of claim 1 wherein said low-emitting regions are substantially perpendicular to said scanning beam line.

* * * * *